United States Patent [19]

Zeller et al.

[11] Patent Number: 4,521,438

[45] Date of Patent: Jun. 4, 1985

[54] COFFEE EXTRACT DECAFFEINATION METHOD

[75] Inventors: Bary L. Zeller, Pleasantville, N.Y.; William W. Kaleda, Westwood, N.J.; Fouad Z. Saleeb, Pleasantville, N.Y.

[73] Assignee: General Foods Corporation, White Plains, N.Y.

[21] Appl. No.: 537,143

[22] Filed: Sep. 29, 1983

[51] Int. Cl.$^3$ ................................ A23F 5/22
[52] U.S. Cl. .................... 426/271; 426/422; 544/274
[58] Field of Search .............. 426/271, 422; 544/274-275

[56] References Cited

U.S. PATENT DOCUMENTS

| | | | |
|---|---|---|---|
| 950,357 | 2/1910 | Trillich | 544/274 X |
| 953,073 | 3/1910 | Trillich | 544/274 X |
| 4,113,887 | 9/1978 | Kramer et al. | 426/422 |
| 4,113,888 | 9/1978 | Heuig et al. | 426/422 |
| 4,315,036 | 2/1982 | Husaini et al. | 426/422 X |
| 4,331,694 | 5/1982 | Izod | 426/422 |

OTHER PUBLICATIONS

Horman et al., The Nature and Conformation of the Caffeine-Chlorogenate Complex of Coffee, Journal of Food Science, 37 (1972), pp. 925-927.

*Primary Examiner*—Joseph Golian
*Attorney, Agent, or Firm*—Thomas A. Marcoux; Daniel J. Donovan; Richard L. Crisona

[57] ABSTRACT

A method of decaffeinating caffeine-containing liquids and particularly aqueous coffee extracts is disclosed. Caffeic acid is added to a caffeine-containing aqueous coffee extract so as to form an insoluble, colloidal caffeic acid/caffeine complex. Crystals of the insoluble caffeic acid/caffeine complex are then grown and subsequently separated from the aqueous decaffeinated coffee extract. The coffee extracts intended for use herein include both roasted and green coffee extracts.

12 Claims, No Drawings

COFFEE EXTRACT DECAFFEINATION METHOD

TECHNICAL FIELD

The present invention relates to a method of decaffeinating caffeine-containing liquids and particularly aqueous coffee extracts. More particularly, the invention involves combining caffeic acid with a caffeine-containing coffee extract to form an insoluble, colloidal caffeic acid/caffeine complex. Crystals of the caffeic acid/caffeine complex are then grown and subsequently separated from the decaffeinated coffee.

BACKGROUND ART

Numerous decaffeination techniques abound in the art. One widely used method is the so-called water decaffenination technique disclosed in U.S. Pat. No. 2,309,092 to Berry et al. In the water decaffeination method, hydrated green coffee beans are extracted with a caffeine-deficient green coffee extract in a multi-stage countercurrent extraction battery. As the green coffee extract progresses through the battery, it becomes increasingly rich in caffeine while contacting decreasingly decaffeinated coffee beans. The caffeine-laden coffee extract withdrawn from the last stage of the battery is treated to remove the caffeine therefrom and subsequently returned to the system. The caffeine is removed from the green coffee extract by contact with an organic solvent, typically a halogenated organic solvent, such as methylene chloride. While the water decaffeination technique enjoys wide application, it is becoming increasingly desirable to avoid the use of organic solvents in food processing. Moreover, the water decaffeination technique is directed to green coffee beans and is not suited to the decaffeination of a roasted coffee extract.

Additional decaffeination techniques exist, but not without drawbacks. For example, the use of a sugar-loaded activated carbon adsorbent is disclosed in European Patent No. 0,008,398 granted May 19, 1982. While the use of an organic solvent is avoided, the activated carbon adsorbent tends to adsorb non-caffeine coffee solubles as well as the caffeine, severely impairing the economy of the method. In addition, the flavor of the finished coffee is not quite the same as that obtained with water decaffeination.

A complexation approach, only with respect to the decaffeination of an aqueous tea extract, is disclosed in U.S. Pat. No. 4,315,036 to Husiani et al. An aqueous tea extract is cooled to precipitate out the cold-water-insoluble complex of caffeine and tannins that are already present in the tea. The method has the advantage of using a complexing compound that is already present in tea and does not then have to be added. Although the tannin/caffeine complex may well be insoluble and therefore precipitate out, such tannins are not present in aqueous coffee extracts.

Many compounds, some native to coffee, are known to complex with caffeine. For example, I. Horman and R. Viani, in "The Nature and Conformation of the Caffeine-Chlorogenate Complex of Coffee" J. Food Sci. 37 (1972) 925–27, recognize ten such caffeine complexes, including the well-studied, water soluble chlorogenic acid/caffeine complex. While it had earlier been speculated that the complexing compounds might be useful in a decaffeination method if it formed a water-insoluble caffeine complex, no such compound native to coffee has heretofore been identified. Moreover, any such native complexing compound would have to compete with the chlorogenic acid and/or break the relatively strong chlorogenic acid/caffeine complex.

DISCLOSURE OF THE INVENTION

A method of decaffeinating caffeine-containing liquids and particularly aqueous coffee extracts has now been found which uses caffeic acid, a caffeine-complexing compound that is native to coffee, particularly roasted coffee. Caffeic acid is combined with caffeine-containing extract to form an insoluble, colloidal caffeic acid/caffeine complex. Crystals of the caffeic acid/caffeine complex are then grown and subsequently separated from the decaffeinated coffee extract.

Caffeic acid is a yellow crystalline material which begins to soften at about 195° C. It is only sparingly soluble in water at less than about 25° C. but freely soluble in water at greater than about 80° C. and freely soluble in alcohol across a wide range of temperatures. The caffeic acid/caffeine complex, however, was unexpectedly found to be insoluble in aqueous solutions over a wide range of temperatures. Although caffeic acid has been reported as high as 0.5% by weight of a roasted and ground coffee, it has now been found that in actuality, caffeic acid is present in only slight amounts in green coffee and in relatively greater but still small amounts in roasted coffee, comprising only about several hundred parts per million of the roasted coffee beans or a typical soluble coffee powder. The greater amount of the acid in roasted coffee results from caffeic acid being one of the roasting breakdown products of the more abundant chlorogenic acid. The caffeic acid used in the present invention may be chemically synthesized but is most preferably obtained from roasted coffee or by the acid hydrolysis of chlorogenic acid so that the decaffeination takes place with compounds native to coffee.

Caffeic acid is particularly suitable because it forms the insoluble complex despite the presence of large amounts of chlorogenic acid in the coffee extracts and despite the caffeic acid/caffeine complex having a lower association constant than the chlorogenic acid/caffeine complex. Horman et al., in the hereinabove cited article, report an association constant of 16.9 for the chlorogenic acid/caffeine complex and an association constant of 12.2 for the caffeic acid/caffeine complex. Inasmuch as the association constant is a measure of the relative strength of the complex, it is most surprising that the added caffeic acid is able to break the chlorogenic acid/caffeine complex undoubtedly already present in the coffee extract and subsequently form the insoluble, colloidal caffeic acid/caffeine complex. Such a result would not be expected based on the reported association constants.

The caffeic acid is combined with the caffeine-containing liquid, most typically an aqueous coffee extract, in order to form an insoluble, colloidal caffeic acid/caffeine complex. The acid, as hereinabove noted, is a solid at typical ambient temperatures and only sparingly soluble in water at those same temperatures. The solid caffeic acid may be combined with the coffee extract and subsequently dissolved therein. Alternatively, it is possible to first prepare an aqueous solution of caffeic acid, preferably at a temperature above 80° C., and combine the caffeic acid solution with the aqueous coffee extract. The coffee extract is diluted somewhat according to the latter embodiment but the increased evaporation load to restore the original concentration is somewhat offset by the ease with which the caffeic acid and aqueous coffee extract are combined.

The temperature at which the caffeic acid is combined with the aqueous coffee extract is not a controlling factor, being bounded by the solubility of the caffeic acid at lower temperatures and the sensitivity of the coffee extract to higher temperatures. It is well known that coffee extracts, green or roasted, tend to degrade in flavor and otherwise at temperatures much above 95° C. Preferably then, the temperature is maintained below about 95° C. when the caffeic acid and the aqueous coffee extract are combined. At the other end of the range, caffeic acid is only sparingly soluble in water or coffee extract at temperatures below about 25° C. and so, it is not convenient to operate at temperatures much below that. The solubility of caffeic acid increases considerably at about 50° C. In the event that an aqueous solution of caffeic acid is first prepared, it is best to dissolve the caffeic acid at a temperature between about 50° C. and 95° C. and combine the solutions with an aqueous coffee extract within or below the same temperature range. In the case where the caffeic acid is dissolved directly in the coffee extract, it is preferred to maintain the extract between 50° C. and 95° C.

A more significant parameter is the mole ratio of caffeic acid to caffeine. Ideally, it is best to combine the caffeic acid with the aqueous coffee extract at a 1:1 mole ratio of caffeic acid to caffeine so that all of the added caffeic acid complexes with the caffeine and is eventually separated as the crystals. This way, preferably essentially all of the caffeine will be removed and there will be no excess caffeic acid left in the decaffeinated coffee extract. In practice, it is difficult to remove essentially all of the caffeine from the coffee extract, with anywhere from 70% to 98% by weight of the caffeine most typically being removed. In addition, it is not convenient to have the mole ratio as low as 1:1 because the kinetics of the complex formation and subsequent crystal growth are not favored by such a ratio. It has been found that a mole ratio of at least 1:1 is desirable with a mole ratio of about 1.5:1 caffeic acid to caffeine being particularly preferred. There is no upper limitation on the mole ratio but it has been found that a ratio much above 3:1 does not give any particular advantage. A ratio closer to 3:1 caffeic acid to caffeine is used with higher pH extracts, owing to the greater solubility of caffeic acid at a higher pH. Substantially all of the remaining caffeic acid that does not complex with cafeine is easily later rendered insoluble and separated out by lowering the temperature of the extract to about 10° C.

Once the caffeic acid has been combined with the caffeine-containing extract so as to form the insoluble, colloidal caffeic acid/caffeine complex, it is necessary to grow the crystals of the insoluble caffeic acid/caffeine complex. The insoluble, colloidal complex forms nearly instantaneously upon the combination of the caffeic acid and coffee extract but, it is exceptionally difficult to separate the colloidal complex from the coffee extract. It has unexpectedly been found though, that the colloidal complex will grow into crystals that are more easily separated from the decaffeinated coffee extract. The crystals will grow of themselves upon standing but the process is slow requiring upwards of two weeks to achieve 65% decaffeination of an aqueous roasted coffee extract. The growth of the crystals is aided somewhat by maintaining the temperature of the coffee extract between about 0° C. and 50° C. Thus, if the temperature of the extract is much above 50° C. for the combination of the caffeic acid and aqueous coffee extract, then the extract containing the insoluble, colloidal caffeic acid/caffeine complex should preferably be cooled so as to aid in the growth of the crystals. Crystal growth is also made more rapid by the known technique of "seeding" with some caffeic acid/caffeine complex crystals that have already formed. The proper level of seeding depends on the particular coffee extract used and will be readily apparent to a worker skilled in the art after one or two trials.

It has also been found that lowering the pH of the caffeine-containing extract promotes the growth of the insoluble caffeic acid/caffeine complex crystals. The pH of coffee extract typically ranges between 4.7 and 5.2. Adding a sufficient amount of acid to lower the extract pH to about 4.5 or below has been found to speed the crystal growth. A pH much below 3.5 however, tends to irreversibly degrade the coffee extracts and so, is not the most desirable. Suitable acids include the strong mineral acids such as hydrochloric acid, sulphuric acid, phosphoric acid and nitric acid as well as the weaker organic acids, including formic acid and acetic acid. Carbon dioxide injected into the coffee extract under pressure also serves to lower the pH, promoting crystal growth. The pH may be adjusted either before or after the combination of the coffee extract with the caffeic acid. The coffee extract can be restored to the original pH after decaffeination. The mineral acids are conveniently precipitated out as salts and the more volatile organic acids are easily steam stripped from the decaffeinated coffee extract.

Various equipment can be used for both combining the caffeic acid and caffeine-containing coffee extract as well as growing the insoluble caffeic acid/caffeine complex crystals. The simplest processing equipment is an agitated batch tank with a means for controlling the temperature of the contents such as by jacketing the tank. The caffeine-containing coffee extract is first added to the tank and adjusted to the desired temperature. The caffeic acid is then added as either a solid or in solution while gently agitating the tank contents. The temperature is then readjusted to promote crystal growth and the crystal seeds are added. The contents are allowed to stand under gentle agitation for a fixed period of time depending on the desired degree of decaffeination and the particular aqueous coffee extract. The tank is then drained and the coffee extract containing the insoluble caffeic acid/caffeine complex crystals is passed to a suitable separation apparatus. Alternatively, the method of the present invention may be continuous, with the decaffeination taking place in an elongated colum. The caffeine-containing coffee extract and caffeic acid are introduced into the bottom of the column which may be maintained at a higher temperature than the rest of the column by the suitable use of separate column jackets. The insoluble caffeic acid/caffeine complex crystals grow as the extract is pumped to the top of the column, whereupon, the extract is removed for separation of the complex crystals.

Separation of the insoluble caffeic acid/caffeine complex crystals from the decaffeinated coffee extract may be by any of the solid/liquid separation techniques known in the art. Filtration of the crystals is one example. Most preferably, the insoluble caffeic acid/ caffeine complex crystals are separated from the coffee extract by centrifugation. Such centrifugation is relatively simple, efficient and not particularly costly. Moreover, centrifugation provides a relatively "clean" separation so that the decaffeinated coffee extract is essentially free of the complex crystals and the separated crystals have only a negligible amount of entrained coffee extract, cutting losses of the economically valuable coffee extract. Even so, it may be desirable to rinse the separated complex crystals with chilled water to recover any entrained non-caffeine coffee solubles.

Although the insoluble caffeic acid/caffeine complex crystals may simply be disposed of after separation, both the caffeic acid and caffeine are costly and worth recovering. Recovery may be by dissolving complex crystals in a solvent capable of both dissolving and breaking the complex. Suitable solvents include the lower boiling alcohols such as methanol, ethanol, or propanol as well as other solvents such as acetone or ethyl acetate. The separated caffeic acid/caffeine complex crystals are dissolved in the solvent, breaking the complex and thus permitting the separate recovery of caffeic acid and the caffeine. The separate recovery may be effected by adsorption of one component onto an adsorbent specific to that component or extraction with a solvent specific to one component.

The method of the present invention is applicable to caffeine-containing liquids and most particularly, to aqueous coffee extracts of both roasted and green coffee. The green coffee extract contemplated for use herein is one deriving from the hereinbefore described water decaffeination process and typically contains between 20% and 35% by weight coffee solubles and from 0.5% to 1% by weight caffeine. The present invention replaces the solvent for the removal of caffeine in the water decaffeination process, eliminating a drawback of that technique. The instant method is also useful for decaffeinating extracts of roasted coffee such as those typically used in the manufacture of soluble coffee. Such a roasted coffee extract most often contains from 10% to 30% by weight coffee solubles and from 0.5% to 5% by weight caffeine. The key advantage of the present invention with regard to roasted coffee extracts is the absence of any impairment or loss of the desirable roasted coffee flavor and aroma. Inasmuch as it is typically desirable to remove in excess of 97% of the caffeine initially present from either the green or roasted coffee extract though, it may be necessary to repeat the method of the present invention more than one time for any given coffee extract, depending on the desired degree of decaffeination.

The following examples are meant to illustrate certain embodiments of the present invention. The examples are not intended to limit the invention beyond what is claimed below.

EXAMPLE 1

An aqueous, equimolar solution of chlorogenic acid and caffeine was prepared by combining 30.0 g water, 1.65 g chlorogenic acid and 0.9 g caffeine. The solution was heated to near boiling. An equimolar portion of caffeic acid weighing 0.85 g was added to and dissolved in the hot solution. The solution was allowed to cool to ambient temperature. Crystal growth was observed after about one hour. After 12–14 hours, the crystals were filtered from the solution using a coarse filter paper. Subsequent analysis showed that approximately 93% of the caffeine was removed whereas no measurable amount of chlorogenic acid was removed.

The analysis for caffeine in this and the following examples was carried out by high performance liquid chromatography (HPLC), with the removal of caffeine being measured by the change in area of the peak identified as caffeine. A Resolve Column (5$\mu$ spherical $C_{18}$; 3.9 mm $\times$ 15 cm) was used at a wavelength of about 280 nm for caffeine and caffeic acid. The mobile phase consisted of 0.0033 M $KH_2PO_4$, methanol and acetic acid at a ratio of 80:20:4 parts respectively. The analysis was made at ambient temperature, isocratically, with a flow rate of 1.5 ml/min and an injection volume of 5 $\mu$l. The solutions were diluted to 0.1% by weight total solids using the mobile phase prior to analysis.

EXAMPLE 2

An aqueous solution was prepared by dissolving 0.9 g of caffeic acid in 90.0 g of near boiling water. Next, 10.0 g of a dried atmospheric coffee extract containing 9.5% by weight caffeine was dissolved in the solution. A control sample was prepared by dissolving 10.0 g of the coffee in 90.0 g of water. Both coffee solutions were allowed to cool. Crystals were observed in the solution containing the caffeic acid after 12–14 hours. No crystals were observed in the control sample. After 1 week, further crystal growth was observed in the solution containing the caffeic acid and the supernatant solution was decanted from the crystals and the solution was allowed to stand for another week. A small portion of the solution was analyzed and found to contain about 30% less caffeine than originally. No crystals were observed in the control sample. After the second week, crystal growth was again observed in the solution containing caffeic acid. The supernatant solution was decanted from the crystals. A small portion of the solution was analyzed and found to contain about 65% less caffeine than originally. The crystals were analyzed and found to be essentially pure 1:1 molar caffeic acid/caffeine complex. No crystals were observed in the control sample which, upon analysis, was found to have all the caffeine initially present.

EXAMPLE 3

A 10% by weight coffee solution was prepared from a dried atmospheric coffee extract containing 8.7% by weight caffeine. The solution was subdivided into 4 parts which were then heated to 70° C. Caffeic acid was added to three of the samples at a ratio of 1:1:1 moles caffeic acid to caffeine. The four samples were then cooled to 40° C. Acetic acid was added to two of the caffeic acid-containing samples to lower the pH of the first to 4.5 and the pH of the second to 4.2. The 4 samples were stirred at 40° C. and periodically subsampled. The results are shown in the Table below.

TABLE

| Sample | Acetic Acid | pH | % decaffeination 24 hours | 5 days |
|---|---|---|---|---|
| 1 (control-no caffeic acid) | No | 5.1 | — | — |
| 2 | No | 4.9 | 9 | 54 |
| 3 | Yes | 4.5 | 49 | 64 |
| 4 | Yes | 4.2 | 64 | 70 |

After 5 days, the crystals were filtered from samples 2–4 using ultracentrifugation at 350,000 g's for 30 minutes. The crystals were analyzed and found to be essentially pure 1:1 molar caffeic acid/caffeine complex. No crystals were observed in the control sample, sample 1.

What is claimed is:

1. A method of decaffeinating a caffeine-containing coffee extract which comprises:
   (a) combining caffeic acid with a caffeine-containing coffee extract so as to form an insoluble colloidal, caffeic acid/caffeine complex;
   (b) growing crystals of the insoluble caffeic acid/caffeine complex which can be separated from the liquid;
   (c) separating the insoluble caffeic acid/caffeine complex crystals from the decaffeinated liquid.

2. A method as in claim 1 wherein the caffeine-containing coffee extract is an extract of green coffee.

3. A method as in claim 1 wherein the caffeine-containing coffee extract is an extract of roasted coffee.

4. A method as in claim 1 wherein the caffeic acid is combined with the caffeine-containing coffee extract at a mole ratio of at least 1:1 caffeic acid to caffeine.

5. A method as in claim 1 wherein the caffeic acid is combined with the caffeine-containing coffee extract as a solid and subsequently dissolved in the coffee extract.

6. A method as in claim 1 wherein the caffeic acid is combined with caffeine-containing coffee extract as an aqueous solution.

7. A method as in claim 6 wherein the caffeic acid solution is combined with the caffeine-containing coffee extract at a temperature from 50° C. to 95° C.

8. A method as in claim 7 which further comprises cooling the caffeic acid and coffee extract combination to a temperature from 0° C. to 50° C. to promote growth of the insoluble caffeic acid/caffeine complex crystals.

9. A method as in claim 2 or 3 which further comprises adding an acid to the coffee extract in order to lower the pH to below pH 4.5.

10. A method as in claim 1 wherein the insoluble caffeic acid/caffeine complex crystals are separated from the coffee extract by centrifugation.

11. A method as in claim 1 which further comprises dissolving the caffeic acid/caffeine complex crystals after separation from the coffee extract so as to break the caffeic acid/caffeine complex and then separately recovering the caffeic acid and caffeine.

12. A method as in claim 11 wherein the solvent used to dissolve the caffeic acid/caffeine complex crystals is selected from the group consisting of methanol, ethanol, propanol, ethyl acetate and acetone.

* * * * *